(12) United States Patent
Inglese et al.

(10) Patent No.: US 8,503,604 B2
(45) Date of Patent: Aug. 6, 2013

(54) PANORAMIC DENTAL RADIOLOGY APPARATUS AND ASSOCIATED METHOD OF USE

(75) Inventors: Jean-Marc Inglese, Bussy-Saint-Georges (FR); Vincent Loustauneau, Fontenay-Sous-Bois (FR); Sylvie Bothorel, Paris (FR)

(73) Assignee: TROPHY, Croissy Beaubourg (FR)

( * ) Notice: Subject to any disclaimer, the term of this patent is extended or adjusted under 35 U.S.C. 154(b) by 0 days.

(21) Appl. No.: 12/546,137

(22) Filed: Aug. 24, 2009

(65) Prior Publication Data

US 2010/0074403 A1    Mar. 25, 2010

(30) Foreign Application Priority Data

Aug. 22, 2008 (FR) ..................... 08 55685

(51) Int. Cl.
*A61B 6/14* (2006.01)
*H05G 1/02* (2006.01)

(52) U.S. Cl.
USPC ................... 378/40; 378/19; 378/38; 378/39; 378/191; 378/196; 378/197

(58) Field of Classification Search
USPC ................ 378/19, 20, 38, 191, 196, 197, 39, 378/40
See application file for complete search history.

(56) References Cited

U.S. PATENT DOCUMENTS

| | | | | |
|---|---|---|---|---|
| 4,985,907 A | * | 1/1991 | Moteni | 378/39 |
| 5,600,699 A | * | 2/1997 | Suzuki et al. | 378/38 |
| 5,677,940 A | * | 10/1997 | Suzuki et al. | 378/38 |
| 6,118,842 A | * | 9/2000 | Arai et al. | 378/39 |
| 6,224,373 B1 | * | 5/2001 | Lee et al. | 433/172 |
| 6,243,439 B1 | * | 6/2001 | Arai et al. | 378/20 |
| 6,289,074 B1 | * | 9/2001 | Arai et al. | 378/4 |
| 6,493,415 B1 | * | 12/2002 | Arai et al. | 378/4 |

(Continued)

FOREIGN PATENT DOCUMENTS

| | | |
|---|---|---|
| JP | H09122118 A | 5/1997 |
| JP | 2003175031 A | 6/2003 |

(Continued)

OTHER PUBLICATIONS

French search report dated, Mar. 13 2009, from corresponding French application.

(Continued)

*Primary Examiner* — Allen C. Ho
(74) *Attorney, Agent, or Firm* — Young & Thompson

(57) ABSTRACT

A dental radiology apparatus includes an X-radiation generator and a sensor opposite it receiving radiation from the generator. The apparatus produces a panoramic image of an object by displacement of the assembly formed of the generator and the sensor along a given trajectory in a plane, the generator having at least one collimation slit elongated along a z-axis perpendicular to the plane to produce an X-ray beam elongated along this axis in a first mode of operation, the sensor with an array of pixels extending along the Z-axis in correspondence with the beam. The apparatus includes elements for pivoting the sensor by 90° to extend it in a direction parallel to the plane P, switching the generator provided with the collimation slit from the first mode to a second mode of operation to produce an X-ray beam elongated parallel to the direction of the sensor, so that the these positioned sensor is always in correspondence with the beam.

20 Claims, 7 Drawing Sheets

U.S. PATENT DOCUMENTS

| | | | |
|---|---|---|---|
| 6,619,839 B2 * | 9/2003 | Yoshimura | 378/196 |
| 7,136,452 B2 * | 11/2006 | Spartiotis et al. | 378/19 |
| 7,236,563 B2 * | 6/2007 | Sa et al. | 378/39 |
| 7,315,608 B2 * | 1/2008 | Sa et al. | 378/38 |
| 7,336,763 B2 * | 2/2008 | Spartiotis et al. | 378/40 |
| 7,421,059 B2 * | 9/2008 | Suzuki et al. | 378/39 |
| 7,486,767 B2 * | 2/2009 | Sonobe et al. | 378/39 |
| 7,534,038 B2 * | 5/2009 | Rotondo et al. | 378/205 |
| 7,715,526 B2 * | 5/2010 | Spartiotis et al. | 378/39 |
| 7,720,191 B2 * | 5/2010 | Muller | 378/38 |
| 7,773,720 B2 * | 8/2010 | Honjo et al. | 378/19 |
| 7,945,016 B2 * | 5/2011 | Bothorel et al. | 378/38 |
| 8,005,187 B2 | 8/2011 | Suzuki et al. | |
| 8,254,520 B2 * | 8/2012 | Sadakane et al. | 378/38 |
| 2009/0052616 A1 | 2/2009 | Honjo et al. | |
| 2010/0172462 A1 * | 7/2010 | Tancredi et al. | 378/4 |

FOREIGN PATENT DOCUMENTS

| | | |
|---|---|---|
| JP | 2007156706 A | 6/2007 |
| JP | 2007159635 A | 6/2007 |
| WO | 2006/109802 | 10/2006 |
| WO | 2007046372 A1 | 4/2007 |
| WO | 2008/092009 | 7/2008 |
| WO | WO 2008/092009 A3 * | 7/2008 |

OTHER PUBLICATIONS

Lee et al., "Development of a Digital Panoramic X-ray Imaging System for Dental Applications", 2007 IEEE Nuclear Science Symposium Conference Record, M13-193.

* cited by examiner

PANORAMIC DENTAL RADIOLOGY APPARATUS AND ASSOCIATED METHOD OF USE

BACKGROUND OF THE INVENTION

1. Field of the Invention

The present invention relates to a dental radiology apparatus and a method for using this apparatus.

2. Description of the Related Art

In the field of dental radiology, radiology apparatuses are known which comprise an X-ray generator and an X-ray sensor each mounted on an arm with an arch-shaped structure, for example within the framework of acquisitions of panoramic or cone beam tomographic images.

There are apparatuses which allow only panoramic photographs to be taken and others which are capable of producing both panoramic images and cone beam tomographic images.

In the first type of apparatus, the X-ray generator is provided with a vertical collimation slit and the sensor made in the form of an array of pixels is placed behind a vertical slit arranged opposite the slit of the generator.

The object to be radiographed is placed between the X-ray generator and the sensor. The X-rays are emitted by the generator in the shape of a cone collimated by the slit in the direction of the object. The sensor receives the rays that have illuminated the object, converts them into electrical signals and provides at the output an image signal of the illuminated object.

When it is desired to produce, with this type of apparatus, a radiograph of a patient's jaw and in particular to obtain a panoramic image of it, the patient is placed in a sitting or standing position under the arch, between the generator and the sensor.

The arch pivots about a vertical axis of rotation while the jaw is illuminated by the X-rays in order that the sensor can provide image signals of the patient's jaw.

Simultaneously with the rotation movement, the axis of rotation of the arch describes a trajectory in the shape of a horseshoe which follows the shape of the patient's dental arch. The zone of interest under investigation (dental arch) covers the jaw.

However, as the generator and the sensor are placed on either side of the patient, during the rotation bony structures will be superposed on the jaw in the resultant image captured by the sensor.

In order to limit the effects of this superposition, the pixels of the sensor are shifted at a rate which is governed by the movement and position of the arch. This gives rise to a kinetic blurring such that the undesirable bony structures mentioned above manifest themselves in horizontal bands (streaking) which limit the inconvenience when establishing a diagnosis.

Moreover, the procedure is such that the pixels of the sensor which are read shifted in the opposite direction to the movement of travel along the trajectory remain fixed in relation to the plane of the arch located in the clear zone.

This technique, which also contributes to a better dosimetric balance, is known under the name of TDI ("Time Delay Integration").

The combination of the rotational speed of the arch, the trajectory of the center of rotation and the translation speed of the pixels on the sensor allows a focal trough to be obtained which has the shape of a band of greater or lesser width which follows the patient's dental arch. The objects located on either side of this focal trough manifest themselves in streaking.

In the resultant image which presents itself as a developed image of the patient's jaw, the objects located in the focal trough will stand out clearly from the streaking caused by the objects located on either side of this zone, thus facilitating diagnosis.

The displacement of the sensor and the generator along this trajectory is achieved using a servo-motor mechanism (for example an X,Y-controlled table) placed above the arch and controlled to steer the movement along the X- and Y-axes in the plane of rotation of the sensor and the generator.

The control of this mechanism requires knowledge of the trajectory matched to the shape of the patient's dental arch.

When producing panoramic pictures, the operator of the apparatus does not have available information allowing him to control the displacement of the sensor and the generator in a manner suitable for the patient's jaw.

Thus, the apparatus very often makes several standard forms of dental arch available to the operator from which he selects the one that seems to him to be the most suitable for the patient to be radiographed. These standard forms are based on statistical data of typical morphologies. The apparatus is then programmed in order that the assembly formed of the sensor and the generator travels the trajectory corresponding to the selected standard form of arch (the trajectory is defined as being the median line between the two opposite edges of the standard form of the dental arch).

However, this solution is not entirely satisfactory, since the sensor and the generator are not positioned in a manner matched to the morphology of the patient's jaw.

Problems of clarity may result for the zone of interest in the image obtained in this way. For example, the patient's teeth cannot be completely registered in the standard form of arch selected by the operator.

Moreover, the selection process which has just been described requires the operator to carry out several maneuvers in order to obtain a panoramic image which, moreover, is sometimes vague over certain zones of the dental arch (incisors, molars . . . ).

SUMMARY OF THE INVENTION

In the light of the above, it would be useful to have available an apparatus and an associated method which allow at least a partial contribution to the resolution of at least one of the problems described above.

The present invention thus proposes a dental radiology apparatus comprising an X-radiation generator and a sensor opposite it receiving the radiation that has come from the generator, the apparatus being suitable for producing a panoramic image of an object by displacement of the assembly formed of the generator and the sensor along a given trajectory in a plane P, the generator being provided with at least one collimation slit elongated along a Z-axis perpendicular to the plane P so as to produce an X-ray beam elongated along this axis in a first mode of operation, the sensor with an array of pixels being elongated along the Z-axis in correspondence with said beam, characterized in that the apparatus comprises:

means of pivoting the sensor by 90° in order that it is elongated in a direction parallel to the plane P, means of switching the generator provided with the said at least one collimation slit from the first mode of operation to a second mode of operation so as to produce, in this second mode, an X-ray beam elongated parallel to said direction of the sensor, in order that the sensor arranged in this way is always in correspondence with said beam.

The panoramic apparatus fitted with a sensor suitable for the taking of panoramic photographs is therefore equipped with means allowing the sensor to be displaced from its conventional position (panoramic mode) to a position where it will be able to acquire a three-dimensional model of a part of interest of the object by cone beam tomography. Likewise, the apparatus comprises means allowing the mode of operation of the generator provided with the said at least one slit to be subsequently changed, i.e. the elongated orientation of the X-ray beam to be changed. The elongated orientation of the beam must in fact be matched to the orientation of the sensor after pivoting.

This new configuration of a panoramic dental radiology apparatus gives the apparatus a new functionality allowing a three-dimensional model of a specific zone of the object to be obtained (by cone beam tomography). This three-dimensional model will be used by the apparatus when it will operate in conventional panoramic mode in order to produce a panoramic image.

Moreover, the apparatus more particularly comprises:

means of driving in rotation, about a fixed axis of rotation parallel to the Z-axis, the assembly formed of the generator in the second mode of operation and the sensor arranged parallel to the plane P, means of acquiring several image signals of the object illuminated by the collimated radiation for a plurality of angular positions occupied by the generator-sensor assembly during the rotation movement, means of obtaining a three-dimensional model of the illuminated object from the set of acquired image signals, means of identifying, from the three-dimensional model obtained in this way, a trajectory which the generator-sensor assembly will have to follow during the subsequent production of a panoramic image of the object.

In this new configuration (different spatial orientation of the sensor and the X-ray beam produced), the panoramic apparatus comprises means allowing it to obtain, by processing of the data provided by cone beam tomography, a trajectory matched to the object to be radiographed. When a panoramic image of this object is developed, the displacement of the apparatus will be guided along this trajectory in order that the sensor and the generator follow the contours of the object as closely as possible, i.e. as faithfully as possible.

The result is that the panoramic image of the object which will be generated will be of better quality than previously. In fact, it is thus ensured that the object (for example dental arches) is in the focal trough.

Moreover, the operator will not need to choose from standard types of dental arch, which will limit the risk of errors and maneuvers.

According to a characteristic feature, the means of acquiring several image signals comprise means of reading the data captured by the array of pixels of the sensor, said reading means comprising means of grouping the pixels according to a predetermined number of pixels for the purpose of reading the pixels grouped in this way.

The grouping of pixels allows the dose of X-rays used to operate the apparatus to be reduced.

Although spatial resolution is lost in the image acquired during the grouping of pixels, this is not harmful taking account of the sought information.

According to a feature, the means of identifying a trajectory from the obtained three-dimensional model comprise means of thresholding or segmenting the data constituting this three-dimensional model.

According to a feature, the generator is provided with a single collimation slit and is thus able to produce an X-ray beam elongated in a direction parallel to the plane P by pivoting the generator and the slit by 90°.

To this end, the apparatus comprises means (for example a motor) of pivoting, on command, the assembly constituted by the generator and its collimation slit.

According to a feature, the generator is provided with two collimation slits elongated in perpendicular directions which are each able to pass successively, on command, in front of the generator so as to produce an X-ray beam which is elongated along the Z-axis and along an axis perpendicular to the Z-axis respectively.

To this end, the apparatus comprises means (for example a motor) of displacing, on command, the slits and thus positioning the slit having the suitable direction in front of the exit window of the generator in order to produce the slit elongated along the desired axis.

According to a feature, the generator is provided with a single collimation slit, the apparatus comprising means of adjusting the elongation of the slit in directions perpendicular to each other.

Thus, the orientation of the slit in one or other of the directions can be adjusted on command.

It will be noted that the dimensions of the slit can also be adjusted according to need.

According to a feature, the adjustment means are independent as regards the directions.

It is thus possible to choose to elongate the slit in one direction without modifying its elongation in the other direction using the adjustment means specific to each direction.

According to a feature, the collimation slit is delimited by four edges and the adjustment means are able to displace each of the edges independently of one another.

This arrangement thus provides a great flexibility of use and a particularly fine adjustment of the distance between the pairs of opposite edges.

Another object of the invention is a method for producing a panoramic image of an object from a dental radiology apparatus comprising an X-radiation generator and a sensor opposite it receiving the radiation that has come from the generator, the generator being provided with at least one collimation slit elongated along a Z-axis perpendicular to a plane P so as to produce an X-ray beam elongated along this axis in a first mode of operation, the sensor with an array of pixels being elongated along the Z-axis in correspondence with said beam, characterized in that the method comprises the following preliminary steps with a view to operating the apparatus in cone beam tomographic mode in order to obtain a trajectory to be travelled in the plane P by the generator-sensor assembly to produce a panoramic image of the object:

pivoting of the sensor by 90° in order that it is elongated in a direction parallel to the plane P, switching from the first mode of operation of the generator provided with the said at least one collimation slit to a second mode of operation in which an X-ray beam elongated parallel to said direction of the sensor is produced in order that the latter is always in correspondence with said beam.

This method thus provides for the temporary switching from a panoramic mode of operation to a cone beam tomographic mode of operation in order to acquire data which will be used to improve the operation of the apparatus in panoramic mode and, in particular, to increase the quality of the panoramic images.

More particularly, the method comprises the following steps, still prior to the acquisition of a panoramic image:

driving in rotation of the assembly formed of the generator in the second mode of operation and the sensor arranged parallel to the plane P about a fixed axis of rotation parallel to the Z-axis, acquisition of several image signals of the object illuminated by the collimated radiation for a plurality of angular positions occupied by the generator-sensor assembly during the rotation movement, obtaining, from the set of acquired image signals, of a three-dimensional model of the illuminated object, identification, from the three-dimensional model obtained in this way, of a trajectory along which the generator-sensor assembly will move during the subsequent production of a panoramic image of the object.

When the apparatus is used according to a cone beam tomographic mode of operation, it is thus possible to obtain a three-dimensional model of the illuminated object or of a part or zone of interest of it.

In order to avoid damaging the dosimetric balance of the set of operations carried out in order to obtain a panoramic image, the doses necessary to obtain this three-dimensional model are reduced.

This reduction in the dose is made possible by the fact that the three-dimensional model of the object is recorded in a cylinder whose height is too small for the data constituting it to be able to be used for the purpose of diagnosis.

Moreover, the processing operations (thresholding or segmentation) which will be carried out on the data constituting the three-dimensional model of the object (envelope of the object or of part of it) in order to determine the sought trajectory for the panoramic mode of operation do not require a high-quality image.

A reduction of the X-ray doses is thus possible, since it will not prevent this trajectory from being obtained.

The sought trajectory can be defined as being the median line relative to the envelope of the object or of part of the object provided by the aforementioned three-dimensional model.

It will be noted that it is possible to further reduce the X-ray doses used for the cone beam tomographic mode of operation. To do this, the acquisition of several image signals comprises a step of reading the data captured by the array of pixels which provides for the grouping of the pixels of the sensor according to a predetermined number (such that the group of pixels forms a square) for the purpose of reading the pixels grouped in this way.

Thus, by way of example, if the pixels are grouped two-by-two, the signal-to-noise ratio is multiplied by four and the X-ray dose is reduced fourfold.

When the apparatus will subsequently be used according to a panoramic mode of operation, the generator-sensor assembly will move along the trajectory obtained above using the live data of the object, which will guarantee the quality of the panoramic image produced, in particular its clarity.

According to a feature, the method comprises the following steps:

pivoting of the sensor by 90° to bring it into a position parallel to the Z-axis, switching from the second mode of operation of the generator provided with the said at least one collimation slit to the first mode of operation, controlling of the displacement of the assembly formed of the generator provided with the said at least one collimation slit and the sensor arranged parallel to the Z-axis along the previously identified trajectory combined with a rotation movement about an axis parallel to the Z-axis, acquisition of a panoramic image of the object during this controlled displacement combined with a shift of the pixels of the sensor.

It is thus easy to revert to the conventional panoramic mode of operation by activating the 90° pivoting of the sensor and the first mode of operation of the generator provided with the said at least one collimation slit.

The obtained trajectory thus allows the precise and reliable programming of the displacement of the sensor and the generator in the plane in order to produce a final image of high quality.

BRIEF DESCRIPTION OF THE DRAWING FIGURES

Other details and advantages of the invention will appear during the description given below in non-limitative manner with reference to the attached drawings, in which.

Figure 1:
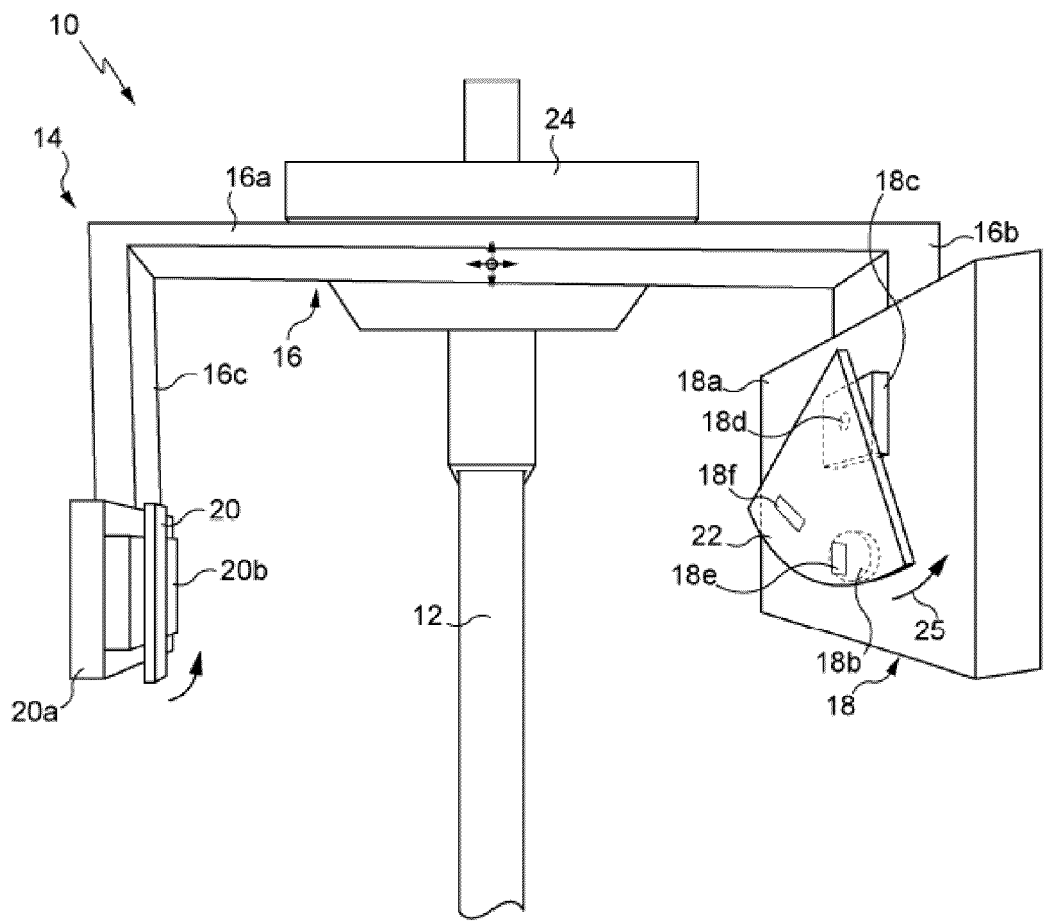
FIG. 1 is a general schematic view of a dental radiology apparatus according to the invention.
Figure 5A:
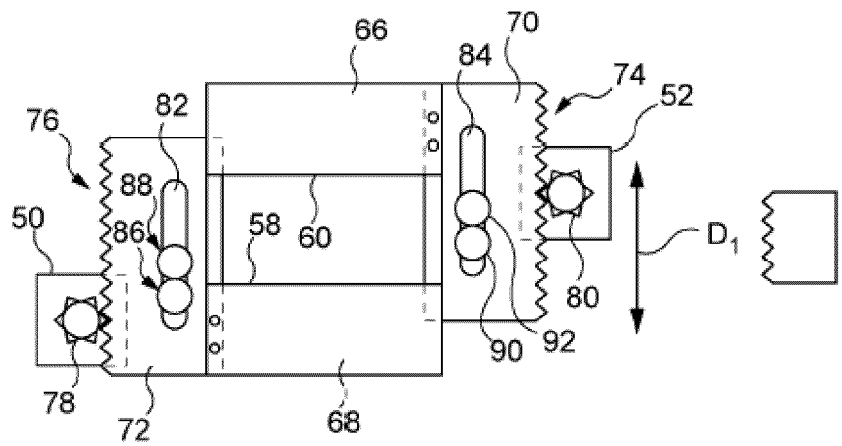
Figure 5B:
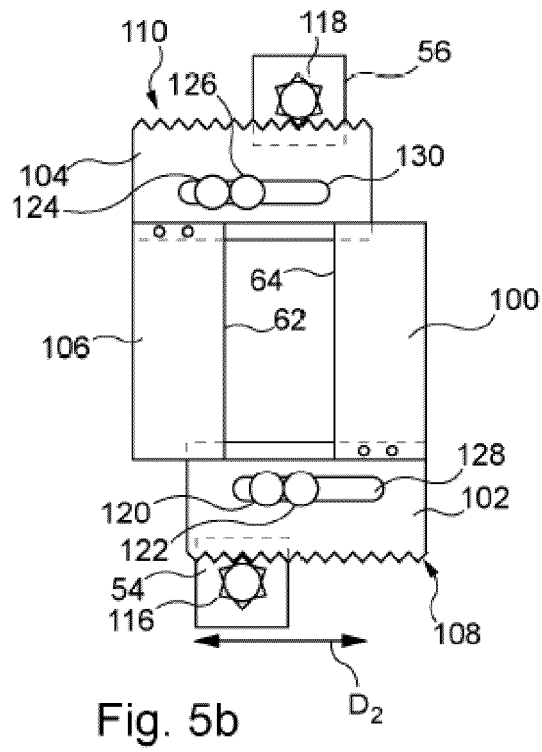
Figure 5C:
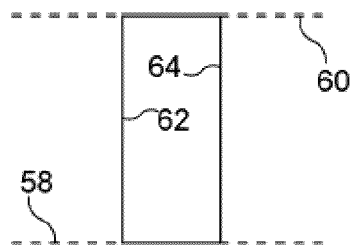
Figure 6:
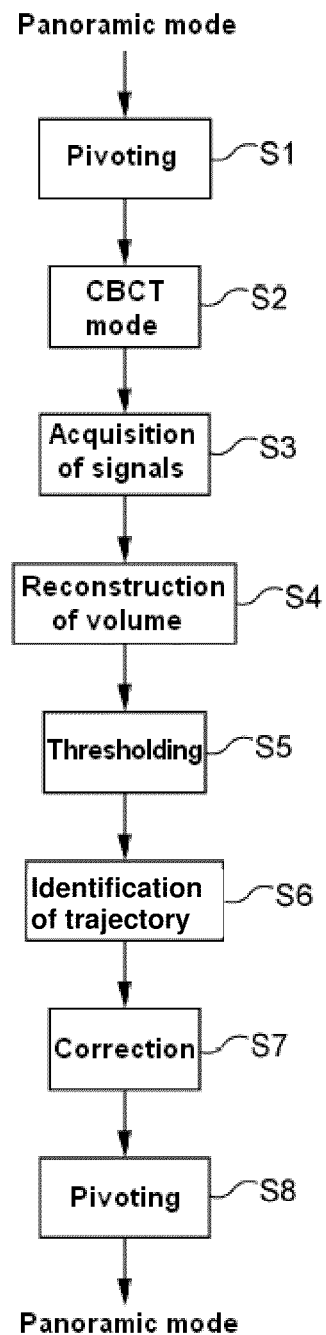
Figure 7:
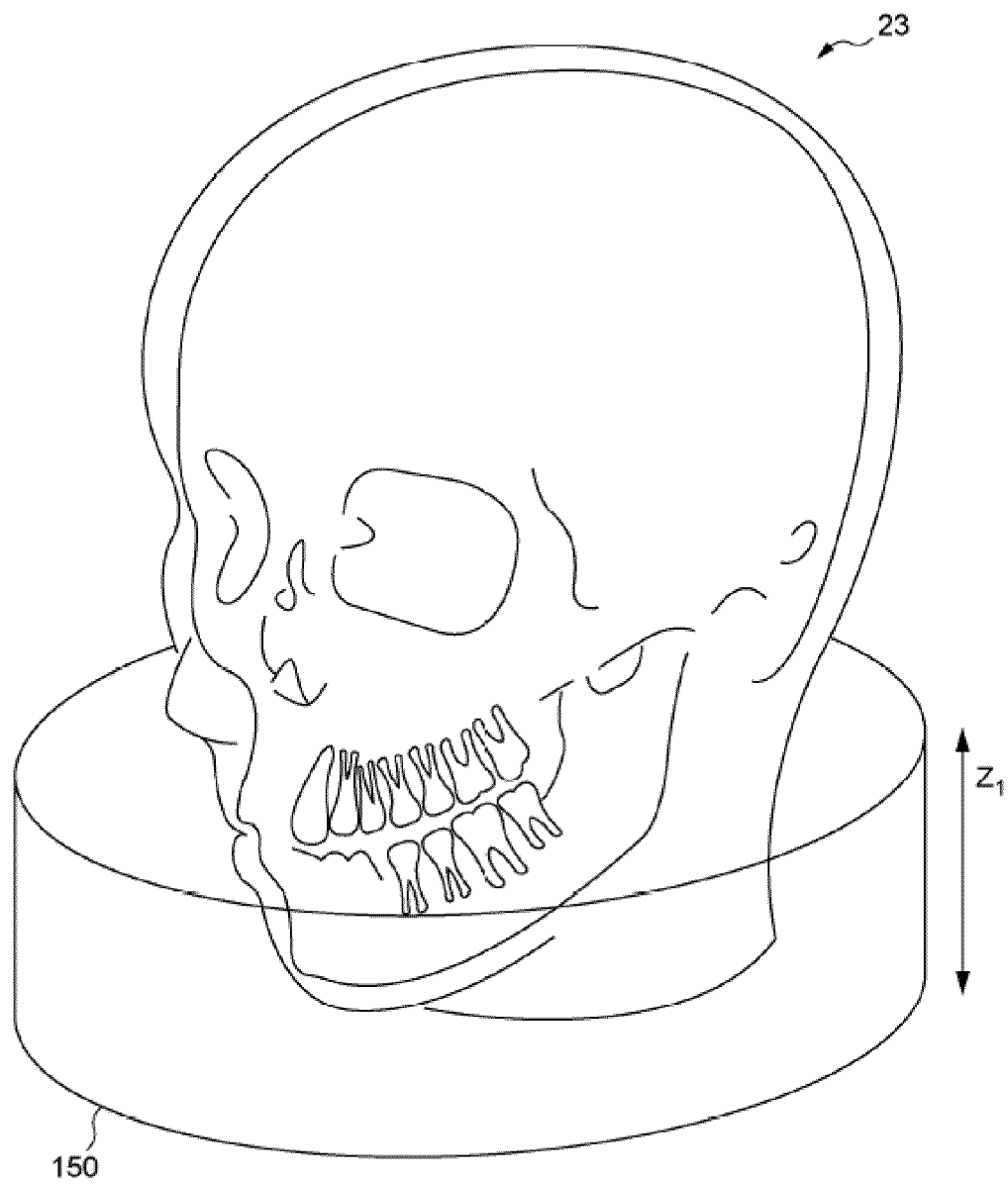
Figure 8:
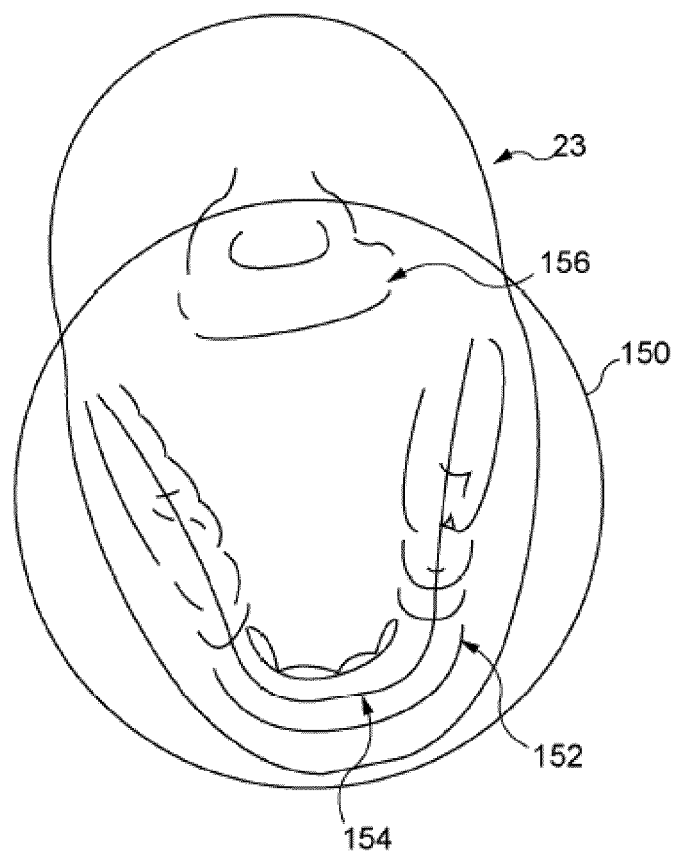
Figure 9:
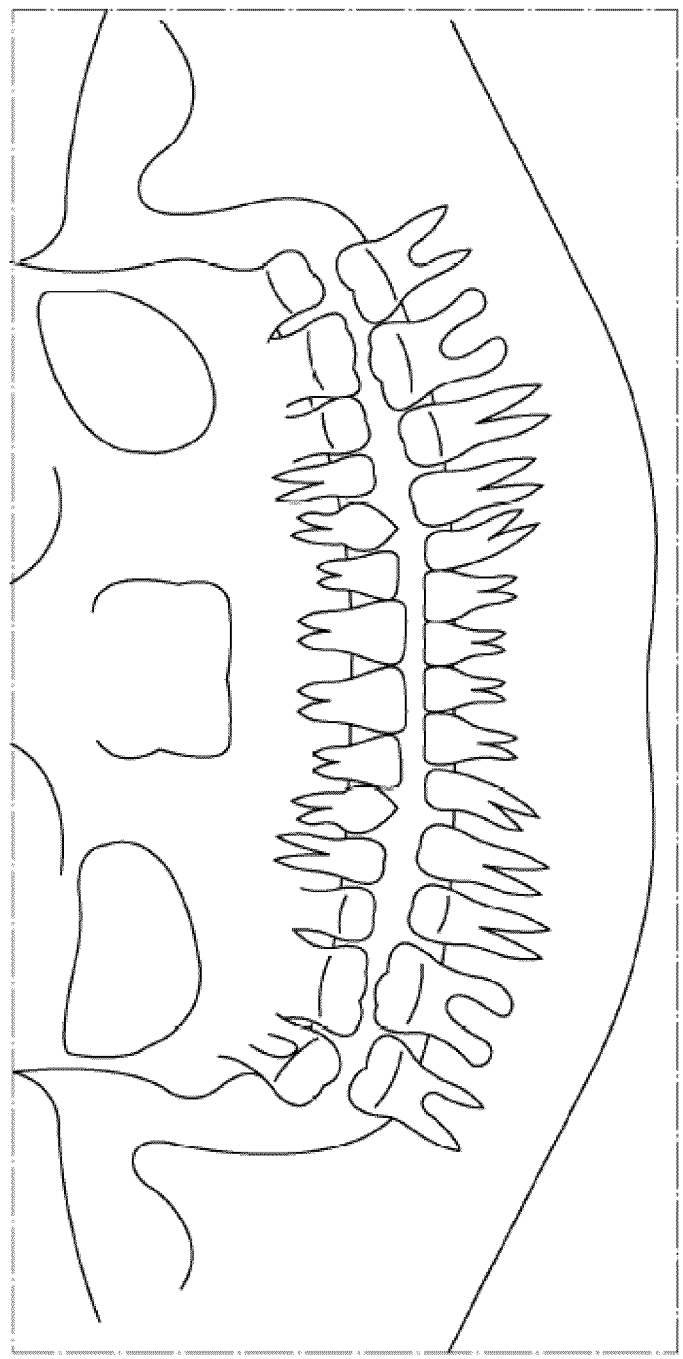

FIGS. 5a and 5b schematically illustrate the means used to create a single variable-geometry slit;

FIG. 5c illustrates an example of a slit obtained with the arrangements of FIGS. 5a and 5b;

FIG. 6 represents an operating algorithm of the apparatus of FIG. 1;

FIG. 7 schematically illustrates the reconstructed volume of a part of the object 23;

FIG. 8 schematically illustrates, seen from above, the dental arch and the trajectory obtained using the invention;

FIG. 9 is a schematic representation of a panoramic image obtained from the trajectory of FIG. 8.

DETAILED DESCRIPTION OF THE INVENTION

As represented in FIG. 1 and designated by the general reference number 10, a dental radiology apparatus according to the invention is an apparatus of the panoramic type. This apparatus allows the production of panoramic images of an object such as a dental arch. The apparatus comprises a fixed column 12, for example a vertical support tube, on which a revolving radiographic unit 14 is mounted which will now be described.

This unit comprises a mobile structure 16 in the form of a flattened C (arch) comprising a horizontal central beam 16a forming a support which constitutes the body of the C and two vertical arms 16b and 16c descending from the horizontal beam and each constituting the two branches of the C.

An X-ray source or generator 18 is mounted in fixed manner on the arm 16b, while an X-ray sensor 20 is mounted on the arm 16c.

The generator 18 and the sensor 20 are thus arranged opposite each other and are in a fixed geometric relation to each other.

The structure 16 which acts as a support for the generator 18 and the sensor 20 constitutes the core of the revolving radiographic unit 14.

The radiology apparatus 10 also comprises, in a manner not represented, a lower arm fixed at one end to the column 12. The free end of the arm is equipped with a positioning device allowing the patient's head to be immobilized while radiographic photographs are taken, during the operation of the apparatus. The head is thus interposed between the generator 18 and the sensor 20.

The radiation generator is equipped with a mobile support 22, for example in the form of a portion of a circle (angular sector), fitted against the face 18a of the generator which faces the sensor 20 and in which an opening 18b is made for the emergence of the X-rays from the generator.

The support is positioned in front of this exit window 18b for the X-rays and comprises several collimation slits, for example two. These slits are intended to each be placed facing the window 18b depending on the controlled displacement of the support.

A displacement means such as a motor 18c allows the displacement of the support which takes place, here in the form of a pivoting about an axis 18d perpendicular to the face 18a of the generator, to be controlled.

In the example represented, the slits are elongated in directions which are perpendicular to each other: when each slit is arranged in turn in front of the window 18b, the slit 18e is vertical and the slit 18f is horizontal.

Each slit is, for example, rectangular in shape.

The collimated X-ray beam thus has the form of a cone which has been truncated by its passage through the slit opposite the rectangular section. This beam is elongated, at its base (in a section parallel to the plane of the slit), in a direction corresponding to the direction in which the slit is elongated.

In the position represented in FIG. 1, the slit 18e which is elongated along the Z-axis has been selected (first mode of operation of the generator).

The sensor 20 attached to the arm 16c is positioned opposite the generator 18. It is able, on the one hand, to receive the X-radiation originating from the generator that has illuminated the object placed between generator and sensor and, on the other hand, to transform this radiation attenuated by its passage through the object into an electrical signal representing a radiographic image of this object.

It will be noted that the sensor comprises an array of pixels which is elongated in a longitudinal direction parallel to the Z-axis (FIG. 1) and arranged to correspond to the beam that has come from the collimation slit 18e for this first mode of operation of the apparatus.

This sensor is, for example, a charge transfer sensor of CCD type and its rectangular dimensions are for example 12 cm (height along the Z-axis)×1 cm (width). An electronics unit 20a controlling and feeding the sensor is provided behind it.

The apparatus of FIG. 1 is able to operate in known manner in panoramic mode (first mode).

Figure 2:
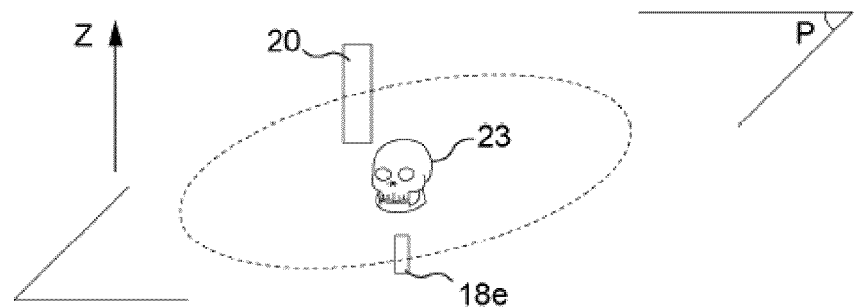
FIG. 2 is a general schematic view showing the arrangement of the sensor and of the vertical slit in position for the panoramic mode of operation.

To do this, the assembly comprising the generator and the sensor carried by the arch-shaped structure carries out a displacement in a plane P perpendicular to the Z-axis which, here, is a horizontal plane (FIG. 2). The operation of the apparatus would, however, be identical if the Z-axis and the plane P, both perpendicular, adopted a different spatial orientation.

The displacement in the plane P is a movement resulting from a combination of an axis of rotation parallel to the Z-axis and a displacement along a trajectory in the shape of a horseshoe which reproduces the general shape of a dental arch of a patient's jaw 23.

This trajectory corresponds, in a horizontal plane, to the median line between the two opposite edges of the dental arch.

The displacement of the generator-sensor assembly is carried out by means of displacement of the load-bearing structure.

These means are, for example, in the form of an X,Y-controlled displacement table 24 (servo-control mechanism) which is programmed to describe the aforementioned trajectory.

Figure 3:
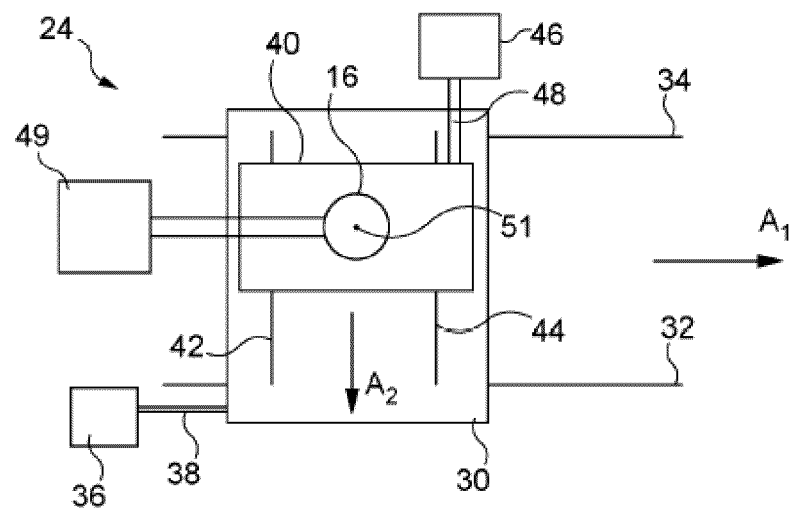
FIG. 3 is a simplified general schematic view of the displacement table 24 of the apparatus of FIG. 1.

As represented very schematically in FIG. 3, the table 24 comprises a first carriage 30 sliding on two longitudinal rails 32, 34 in a first direction A1 (Y) under the action of a first drive means such as a motor 36 connected to the carriage by an endless screw 38.

The table also comprises a second carriage 40 sliding on two longitudinal rails 42, 44 in a second direction A2 (X) (the directions A1 and A2 are contained in a plane parallel to the plane P) under the action of a second drive means such as a motor 46 connected to the carriage by an endless screw 48.

The table 24 is integral with the arch-shaped structure 16 and a drive means 49 such as a motor is connected to the structure 16 in order to drive this structure in rotation, on command, about the axis of rotation 51 perpendicular to the plane P and thus perpendicular to the plane defined by the directions A1 and A2.

By controlling the displacement of the carriages 30 and 40 in a suitable manner in the directions X and Y, the structure 16 describes the sought trajectory (in the shape of a horseshoe) in the plane P.

It will be noted that, during the displacement of the generator and sensor around the object (patient's jaw) in the plane P, the sensor operates in what is called TDI ("Time Delay Integration") mode.

This mode of operation known per se has the aim of functioning such that the pixels of the mobile sensor which capture the radiation that has illuminated the patients jaw are regarded as fixed in relation to the jaw.

To do this, the frequency of reading of the array of pixels is arranged such that the shift of the lines of the array towards the shift register, under the reading pulses of the latter, takes place in a direction opposite to that of the displacement of the sensor.

The TDI mode thus allows the blurring phenomena in the panoramic image obtained to be avoided.

The first mode of operation of the apparatus of FIG. 1 which has just been described relates to the panoramic mode.

The apparatus according to the invention is however capable of being used in a second mode of operation in order to determine a trajectory which will be travelled by the sensor and the generator in the panoramic mode of operation.

Figure 4:
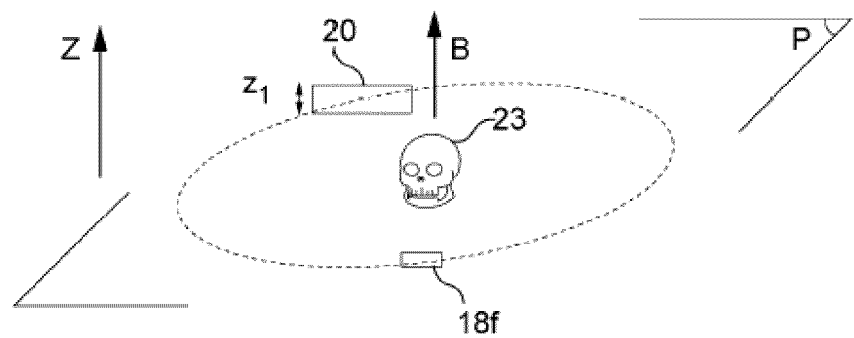
FIG. 4 is a general schematic view showing the arrangement of the sensor and of the horizontal slit in position for the mode of operation for determining a trajectory.

To do this, the apparatus comprises means 20b (for example a motor) for pivoting the sensor 20 of FIG. 2 by 90° in order to bring it into the position illustrated in FIG. 4.

The sensor is thus arranged elongated in a direction parallel to the plane P.

The apparatus also comprises means adapted in order that the X-ray generator provided, in a general manner, with at least one collimation slit switches from the first mode of operation (slit elongated along the Z-axis in FIG. 2) to a second mode of operation in which the slit is elongated in a direction parallel to the plane P and to the longitudinal direction of the sensor.

In this second mode of operation, the generator which is fitted with a slit having such a spatial orientation is capable of producing an X-ray beam elongated, at its base, in this same orientation.

Thus, the sensor and the slit are always positioned opposite each other, such that the X-ray beam can still reach the sensor after pivoting.

In the embodiment of FIG. 1, the radiology apparatus is provided with two collimation slits 18e, 18f which can switch according to the displacement imposed on the drive means 18c of the slit support 22.

By switching the slits (pivoting of the slits support in the direction indicated by the arrow 25), the vertical slit 18e of FIG. 2 is replaced by the horizontal slit 18f which has just positioned itself in front of the exit window 18b.

The sensor 20 and the slit 18f arranged in this way (FIG. 4) will then be driven in rotation about an axis of rotation B (vertical) by the means 49 of FIG. 3 in order to determine the aforementioned trajectory matched to the object 23, as will be explained below.

FIGS. 5a and 5b illustrate a variant allowing a single collimation variable-geometry slit to be produced by replacing the slits 18e and 18f of FIG. 1.

Adjustment means are provided in order to vary, on command, the geometry of the slit and, in particular, its elongation in two directions perpendicular to each other, for example horizontal and vertical.

More particularly, the adjustment means suitable for modifying the elongation of the slit in one direction are independent of those suitable for modifying the elongation in the other direction, thus offering a greater flexibility of adjustment.

In the example illustrated, the radiology apparatus comprises four independent adjustment means 50, 52, 54, 56 for independently varying the position of each of the four edges 58, 60, 62, 64 defining the collimation slit.

The apparatus comprises a slit support, not represented, for example carried by the generator 18 of FIG. 1, or even attached directly to the structure 16 (for example to the arm 16b), which is placed in front of the window 18b.

On this support are superposed, in succession, the arrangement of FIG. 5b, then that of FIG. 5a.

These arrangements have not been represented superposed, for the sake of clarity.

More particularly, the arrangement of FIG. 5a comprises two edges 58, 60 of two plates 66, 68 positioned opposite each other (for example rectangular) which are each fixed to another plate 70, 72 respectively arranged perpendicularly.

Each pair of plates 66, 70 and 68, 72 thus forms an L or an L rotated by 180°.

The second plate 70, 72 of each pair is provided, on one of its edges opposite that against which the first plate is fixed, with a longitudinal row of teeth 74, 76.

A means of displacing the edge 58 (or 60) comprises a motor 50 (or 52) equipped on its output shaft with a toothed pinion 78 (or 80). This pinion cooperates with the teeth 76 (or 74) to initiate the displacement of the plates 72 and 68 in the direction D1 in one or other direction depending on the rotational direction of the pinion.

A guide slot 82 (or 84) is provided in the second plate 72 (or 70) and two guide pins 86, 88 (or 90, 92) integral with the aforementioned support are positioned in this groove in order to longitudinally guide the displacement of the corresponding plate and thus of the corresponding edge.

This arrangement allows, by adjusting the distance between the opposite edges 58 and 60 in the direction D1, the adjustment of one of the dimensions of the slit and thus its elongation in one direction.

In the same way, the arrangement illustrated in FIG. 5b allows, by adjusting the distance between the opposite edges 62 and 64 in the perpendicular direction D2, the adjustment of one of the dimensions of the slit in another direction.

Thus, by bringing the edges 62 and 64 closer together and by moving the edges 58 and 60 further apart, the slit is shaped elongated in the direction D1. A slit elongated along the Z-axis represented in FIG. 5c (like the slit 18e of FIGS. 1 and 2) is thus obtained.

On the other hand, if the edges 62 and 64 are moved further apart and the edges 58 and 60 are brought closer together, the elongated shape of the slit is produced in the direction D2. A slit elongated along an axis perpendicular to the Z-axis like the slit 18f of FIGS. 1 and 4 is thus obtained.

The different elements represented in FIG. 5b, namely the first and second plates 100, 102 (or 104, 106), the grooves 108 (or 110), the motor 54 (or 56) and its toothed pinion 116 (or 118), as well as the guide pins 120, 122 (or 124, 126) in the guide slot 128 (or 130), are identical to the corresponding elements in FIG. 5a but are shifted by only 90°.

The panoramic apparatus 10 which has just been described comprises the means allowing it to produce panoramic images of improved quality compared with the state of the art and its use/mode of operation will now be described.

FIG. 6 represents an algorithm detailing the principal steps of an operating method of the apparatus 10 according to the invention.

This algorithm is for example stored in a storage area of a programmable device (example: a computer of PC type) which controls the operation of the apparatus 10 and is executed on command.

The method according to the invention can advantageously be used automatically, thus limiting human involvement.

The algorithm of the method illustrated in FIG. 6 comprises a first step S1 during which the radiology apparatus leaves the panoramic mode (first mode of operation) and switches to a pivoting mode (second mode of operation).

More particularly, during this step the sensor is automatically driven in rotation by the motor 20b in a 90° pivoting movement from the initial position which it occupies when the apparatus is operating in panoramic mode (FIGS. 1 and 2).

The sensor is thus positioned elongated in a direction parallel to the plane P (FIG. 4). Similarly, the displacement of the slit support 22 is activated in order to bring the slit 18f in front of the window 18b in the second mode of operation of the generator. Thus, the X-ray beam collimated by this slit which is oriented parallel to the plane P and parallel to the sensor is shaped so as to always be in correspondence with the new position of the sensor. The radiation that has come from the generator and been collimated by the slit is therefore always received by the sensor opposite it.

It will be noted that with the variant illustrated in FIGS. 5a and 5b the adjustable slit is transformed in order to switch from that of FIG. 2 (FIG. 5c) to that of FIG. 4 by displacing the edges in an suitable manner, as explained above.

During the following step S2 the radiology apparatus is activated in order to change to CBCT ("Cone Beam Computed Tomography") mode of operation.

It will be noted that the panoramic apparatus is not normally equipped to produce radiographic photographs according to CBCT technology because of the unsuitable shape of its image sensor.

However, the invention will not allow a complete radiographic photograph to be obtained by this technique but will use this mode of operation, temporarily, only to acquire certain personalized data, not accessible in panoramic mode, which will be used subsequently in this mode.

Thus, step S2 is followed by a step S3 of acquiring data in cone beam tomographic (CBCT) mode of operation on the object (for example the object 23 of FIG. 4) placed between the generator and the sensor, and more particularly the patients jaw.

In particular, during step S3 the assembly formed of the generator equipped with its collimation slit and the sensor is driven in rotation in the plane P, about an axis B parallel to the Z-axis. During this rotation movement, this assembly occupies a plurality of successive angular positions for each of which image signals of the object illuminated by the collimated radiation are acquired by the sensor.

During this movement, the center of rotation of the generator-sensor assembly is fixed. This center is for example positioned on the object 23.

For each angular position of this assembly, the data captured by the sensor represent a projection of the object along the generator-image sensor axis.

Thus, at the end of a complete rotation of the generator-sensor assembly, a set of image signals each representing a projection of the object 23 illuminated by the beam for example is obtained and, for example, 360 projections of this object in the case where a photograph is taken for each degree of rotation.

Each analogue image signal is captured by the array of pixels of the sensor, transformed into an analogue electrical signal by the sensor, then converted into a digital signal.

It will be noted that in order to reduce the dose of X-radiation used to obtain these signals, it may be advisable to use the capability of the sensor to group the pixels of the array according to a predetermined number, for example in twos or threes, for the purpose of reading.

In fact, by reading the pixels per group of two or three depending on the chosen grouping ("binning"), the array reading noise is reduced and the signal-to-noise ratio of the sensor is increased, thus allowing the dose of radiation to be reduced.

During the following step S4 the volume of the illuminated part of the object is reconstructed from the set of image signals obtained previously and the reconstructed volume is in the form of a cylinder 150 of small height. The height or thickness of the cylinder z1 corresponds to the smallest dimension of the sensor (width), while the diameter of the cylinder z1, for its part, is limited by the largest dimension of the sensor (length) apart from enlargement coefficients.

By way of example, the height of the cylinder ranges from some hundreds of micrometers to some millimeters.

The volume 150 is represented in FIG. 7 and it surrounds the patient's dental arch.

This reconstructed volume 150 provides a three-dimensional model of the shape of the illuminated object which contains sufficient information to determine the sought data specific to the object.

It will be noted that the three-dimensional model of the object is vertically centered (along the Z-axis) in relation to the zone of interest. This centering is carried out when the generator-sensor assembly is positioned before the assembly is rotated (step S2). The zone of interest in the example described is the "occlusal plane" of the patient's jaw, that is to say the contact interface between the teeth.

During the following step S5 the object or the part of the object of interest, namely in this case the patients dental arch, is defined from the volume reconstructed in this way.

To do this, what is called a "thresholding" or "segmentation" operation is carried out on the data in the reconstructed volume.

The procedure continues, for example by thresholding, by analyzing the differences in the shades of grey between the teeth and their environment which represent differences in density and the shape of the dental arch is deduced from it in three dimensions.

The shape of the dental arch 152 is thus obtained, as represented seen from above in FIG. 8 in which the envelope of the volume 150 is also indicated.

By extracting horizontal sections from the shape of the dental arch 152, the procedure continues during the following step S6 with the determination of the median line 154 which extends, in the dental arch, seen from above, between the opposite edges of this.

The determination of this median line corresponds to the identification of a "trajectory".

More particularly, this median line 154 (FIG. 8) will be used subsequently, when the apparatus will operate in panoramic mode, as a trajectory which the generator and the sensor will travel in order to obtain a panoramic image of the object.

This trajectory in the shape of a horseshoe will allow the panoramic apparatus 10 to be programmed, in a manner matched and personalized to the object. The panoramic apparatuses according to the prior art operate from standard forms of dental arch which are therefore not suitable for the object to be radiographed and are not very precise, unlike the invention.

It will be noted that the thresholding step forms part of the determination of the trajectory.

The trajectory identified in step S6 is sometimes disturbed by different phenomena (metal artifacts such as fillings which are likely to give rise to star-shaped noise around the metal objects, presence of other objects in the field such as the vertebral column 156 in FIG. 8).

In order to improve the accuracy of the trajectory obtained in step S6, a step S7 (optional) correcting this trajectory, for example by smoothing, is provided for.

When the corrected trajectory has been obtained, the following step S8 is carried out, during which the sensor is again driven in a 90° pivoting movement in order to bring it into an orientation parallel to the Z-axis (here, the vertical axis).

Similarly, the displacement of the slits support 22 is activated in order to bring the slit 18e in front of the window 18b of the generator and thus return to the first mode of operation of the generator. The arrangement of the sensor and of the slit of the generator is that of FIG. 2 which has already been described.

After this pivoting step, the panoramic apparatus can thus be programmed anew to operate in panoramic mode.

On this occasion, the trajectory obtained in step S6, optionally corrected in step S7, is used to program the displacement of the assembly formed of the generator provided with the collimation slit and the sensor that have been recently newly positioned parallel to the Z-axis.

During the operation of the apparatus in parameterized panoramic mode with a more suitable trajectory than in the prior art, the assembly formed of the generator and the sensor carries out a rotation movement about its vertical axis of rotation which also moves in a controlled manner along this trajectory using the different drive means illustrated in FIG. 3.

During this displacement, the vertically positioned sensor, operating in TDI mode as explained above, acquires image data of the object (here the arch) illuminated by the radiation which produce the sought panoramic image.

In known manner, a panoramic image of the arch is obtained from the image data acquired by the sensor during the displacement along the trajectory in the shape of a horseshoe.

By combining the movements of rotation of the arch 16, displacement of the center of rotation of the arch using the displacement table 24, sliding of the pixels of the sensor 20 (TDI mode), a virtual rotation point is recreated which is contained at any time in the focal trough. Thus, the anatomical structures located outside this manifest themselves in a streaking which does not harm the diagnosis, and the structures contained in the focal trough appear clear.

FIG. 9 illustrates schematically the panoramic image obtained according to the invention.

It will be noted that the panoramic image obtained in this way has an optimized quality compared with the techniques known according to the prior art, since the panoramic image is here perfectly matched to the object, in this case the morphology of the patient's jaw.

Moreover, the method which has just been described avoids numerous maneuvers by the operator, maneuvers which moreover manifest themselves in inaccurate results.

It will be noted that when the apparatus is operating in CBCT mode the aim is not to obtain a high-quality image using this mode. It is for this reason that the dose of radiation can be reduced in this mode of operation.

The invention claimed is:

1. A dental radiology apparatus comprising:
an x-radiation generator and a sensor opposite the x-radiation generator receiving an x-ray beam that has come from the generator, the apparatus being suitable for producing in a first mode of operation a panoramic image of an object by displacement of an assembly formed of the generator and the sensor along a given trajectory in a plane (P), the generator being provided with at least one collimation slit elongated along a Z axis perpendicular to the plane (P) so as to produce an x-ray beam elongated along the Z-axis in the first mode of operation, the sensor with an array of pixels being elongated along the Z-axis in correspondence with said beam;
means for displacement of the assembly to displace the assembly formed of the generator and the sensor along the given trajectory in the plane (P), the given trajectory of the assembly resulting from a rotation about an axis of rotation that is perpendicular to the plane (P) and displacement of the axis of rotation in the plane (P);
means for pivoting the sensor by 90° in order that the sensor is elongated in a direction parallel to the plane (P);
means for switching the generator provided with the at least one collimation slit from the first mode of operation to a second mode of operation so as to produce, in this second mode, an x-ray beam elongated parallel to said direction of the sensor, in order that the sensor arranged in this way is always in correspondence with said beam;
means for driving in rotation, about a fixed axis of rotation parallel to the axis (Z), the assembly formed of the generator and the sensor in the second mode of operation and the sensor arranged parallel to the plane (P);
means for acquiring several image signals of the object illuminated by an x-ray beam for a plurality of angular positions occupied by the generator-sensor assembly during a rotation movement;
means for obtaining a three-dimensional model of the illuminated object from the acquired image signals; and
means for identifying, from the three-dimensional model, a trajectory which the generator-sensor assembly will have to follow during a subsequent production of a panoramic image of the object.

2. The apparatus according to claim 1, wherein the means for acquiring several image signals comprise means of reading the data captured by the array of pixels of the sensor, said reading means comprising means of grouping the pixels according to a predetermined number of pixels for the purpose of reading the pixels grouped in this way.

3. The apparatus according to claim 2, wherein the means for identifying a trajectory from the obtained three-dimensional model comprise means for thresholding or segmenting the data constituting this three-dimensional model.

4. The apparatus according to claim 1, wherein the means for identifying a trajectory from the obtained three-dimensional model comprise means for thresholding or segmenting data constituting this three-dimensional model.

5. The apparatus according to claim 1, wherein the at least one collimation slit comprises a single collimation slit and is able to produce an x-ray beam elongated in a direction parallel to the plane (P).

6. The apparatus according to claim 1, wherein the at least one collimation slit comprises two collimation slits elongated in perpendicular directions which are each able to pass successively, on command, in front of the generator so as to produce an x-ray beam which is elongated along the Z-axis and along an axis perpendicular to the Z-axis respectively.

7. The apparatus according to claim 1, wherein the at least one collimation slit comprises a single collimation slit, the apparatus further comprising means for adjusting an elongation of the slit in directions perpendicular to each other.

8. The apparatus according to claim 7, wherein the means for adjusting are independent as regards the directions.

9. The apparatus according to claim 8, wherein the single collimation slit is delimited by four edges and the means for adjusting is able to displace each of the edges independently of one another.

10. The apparatus according to claim 7, wherein the single collimation slit is delimited by four edges and the means for adjusting is able to displace each of the edges independently of one another.

11. The apparatus according to claim 1, wherein the apparatus obtaining in the second mode of operation further comprising a means for obtaining a trajectory and means for moving the assembly along the trajectory to acquire a panoramic image that the generator-sensor assembly will have to follow during the subsequent production of a panoramic image of the object when the apparatus is in the first mode of operation.

12. The apparatus according to claim 1, wherein the displacement of the axis of rotation is configured to be relative to a patient's head.

13. A method for producing a panoramic image of an object from a dental radiology apparatus comprising an x-radiation generator and a sensor opposite the x-radiation generator receiving an x-ray beam that has come from the generator, the generator being provided with at least one collimation slit elongated along an axis (Z) perpendicular to a plane (P) so as to produce an x-ray beam elongated along the axis in a first mode of operation, the sensor with an array of pixels being elongated along the axis (Z) in correspondence with said beam, the dental radiology apparatus being suitable for producing a panoramic image of the object in the first mode of operation, the method comprising:
in the first mode of operation, displacing an assembly formed of the generator and the sensor along a given trajectory in the plane (P);
the method further comprises the following preliminary steps:
displacing the assembly along the given trajectory of the assembly resulting from a rotation about an axis of rotation that is perpendicular to the plane (P) and displacement of the axis of rotation in the plane (P);
pivoting the sensor by 90° in order that the sensor is elongated in a direction parallel to the plane (P);

switching from the first mode of operation of the generator provided with the at least one collimation slit to a second mode of operation in which an x-ray beam elongated parallel to said direction of the sensor is produce in order that the sensor is always in correspondence with said beam; and operating the apparatus in the second mode of operation called cone beam tomographic mode in order to obtain a trajectory to be travelled in the plane (P) by the generator-sensor assembly to produce a panoramic image of the object, wherein the method further comprises the following steps:

driving in rotation of the assembly formed of the generator and the sensor in the second mode of operation and the sensor arranged parallel to the plane (P) about a fixed axis of rotation parallel to the axis (Z);

acquiring several image signals of the object illuminated by an x-ray beam for a plurality of angular positions occupied by the generator-sensor assembly during a rotation movement;

obtaining, from the acquired image signals, of a three-dimensional model of the illuminated object; and identifying, from the three-dimensional model, of a trajectory along which the generator-sensor assembly will move during a subsequent production of a panoramic image of the object.

14. The method according to claim 13, wherein the acquiring of several image signals comprises a step of reading the data captured by the array of pixels of the sensor which comprises a grouping of pixels according to a predetermined number of pixels for the purpose of reading the pixels grouped in this way.

15. The method according to claim 14, wherein the identification of a trajectory from the three-dimensional model obtained comprises a step of thresholding or segmenting the data constituting this three-dimensional model.

16. The method according to claim 14, further comprises the following steps:

pivoting of the sensor by 90° to bring it into a position parallel to the axis (Z);

switching from the second mode of operation of the generator provided with the said at least one collimation slit to the first mode of operation;

controlling of the displacement of the assembly formed of the generator provided with the said at least one collimation slit and the sensor arranged parallel to the axis (Z) along the previously identified trajectory combined with a rotation movement about an axis parallel to the axis (Z); and acquiring a panoramic image of the object during this controlled displacement combined with a shift of the pixels of the sensor.

17. The method according to claim 13, wherein the identifying of the trajectory from the three-dimensional model obtained comprises a step of thresholding or segmenting data constituting this three-dimensional model.

18. The method according to claim 17, further comprising the following steps:

pivoting of the sensor by 90° to bring it into a position parallel to the axis (Z);

switching from the second mode of operation of the generator provided with the said at least one collimation slit to the first mode of operation;

controlling of the displacement of the assembly formed of the generator provided with the said at least one collimation slit and the sensor arranged parallel to the axis (Z) along the previously identified trajectory combined with a rotation movement about an axis parallel to the axis (Z); and acquiring a panoramic image of the object during this controlled displacement combined with a shift of the pixels of the sensor.

19. The method according to claim 13, further comprises the following steps:

pivoting of the sensor by 90° to bring the sensor into a position parallel to the axis (Z);

switching from the second mode of operation of the generator provided with the said at least one collimation slit to the first mode of operation;

controlling of the displacement of the assembly formed of the generator provided with the said at least one collimation slit and the sensor arranged parallel to the axis (Z) along the previously identified trajectory combined with a rotation movement about an axis parallel to the axis (Z); and acquiring a panoramic image of the object during this controlled displacement combined with a shift of the pixels of the sensor.

20. The method according to claim 13, wherein the displacement of the axis of rotation is configured to be relative to a patient's head.

* * * * *